(12) United States Patent
Hao et al.

(10) Patent No.: US 10,266,403 B2
(45) Date of Patent: Apr. 23, 2019

(54) HETEROGENEOUS MICROARRAY BASED HYBRID UPCONVERSION NANOPROBE/NANOPOROUS MEMBRANE SYSTEM

(71) Applicant: The Hong Kong Polytechnic University, Hong Kong (CN)

(72) Inventors: Jianhua Hao, Hong Kong (CN); Mo Yang, Hong Kong (CN); Ming-Kiu Tsang, Hong Kong (CN); Weiwei Ye, Hong Kong (CN)

(73) Assignee: The Hong Kong Polytechnic University, Hong Kong (CN)

( * ) Notice: Subject to any disclaimer, the term of this patent is extended or adjusted under 35 U.S.C. 154(b) by 0 days.

(21) Appl. No.: 15/442,850

(22) Filed: Feb. 27, 2017

(65) Prior Publication Data
US 2018/0246084 A1     Aug. 30, 2018

(51) Int. Cl.
| | |
|---|---|
| B82Y 40/00 | (2011.01) |
| C09K 11/77 | (2006.01) |
| B82Y 15/00 | (2011.01) |
| C12Q 1/68 | (2018.01) |
| C12Q 1/6837 | (2018.01) |

(52) U.S. Cl.
CPC ............ B82Y 40/00 (2013.01); B82Y 15/00 (2013.01); C09K 11/77 (2013.01); C12Q 1/68 (2013.01); C12Q 1/6837 (2013.01)

(58) Field of Classification Search
CPC .. G01N 27/403; G01N 33/54346; B82Y 5/00; C07H 21/04
See application file for complete search history.

(56) References Cited

U.S. PATENT DOCUMENTS

| | | | | |
|---|---|---|---|---|
| 2010/0261263 A1* | 10/2010 | Vo-Dinh | ................... | A61L 2/08 435/287.1 |
| 2013/0053260 A1* | 2/2013 | Chen | ................ | G01N 33/54353 506/9 |
| 2016/0250332 A1* | 9/2016 | Punjabi | .............. | C09K 11/7773 604/20 |

OTHER PUBLICATIONS

Ye, W. W. et al, 2014, "Upconversion Luminescence Resonance Energy Transfer (LRET)-Based Biosensor for Rapid and Ultrasensitive Detection of Avian Infl uenza Virus H7 Subtype", Small 10, 2390-2397.
Tsang, M.-K.et al, 2016, "Ultrasensitive Detection of Ebola Virus Oligonucleotide Based on Upconversion Nanoprobe/Nanoporous Membrane System", J. ACS Nano, 10, 598-605.
Wang, Ye-Fu et al., 2013, "$Nd^{3+}$-Sensitized Upconversion Nanophosphors: Efficient In Vivo Bioimaging Probes with Minimized Heating Effect", ACS Nano, 7, 7200-7206.
Li, X. et al, 2016, "Filtration Shell Mediated Power Density Independent Orthogonal Excitations—Emissions Upconversion Luminescence", Angew. Chem. Int. Ed., 2016, 128, 2510-2515.
Deng R. et al, 2011, "Intracellular Glutathione Detection using $MnO2$-Nanosheet-Modified Upconversion Nanoparticles", J. Am. Chem.Soc., 133, 20168-20171.
Huang P. et al, 2014, "Lanthanide-Doped $LiLuF4$ Upconversion Nanoprobes for the Detection of Disease Biomarkers", Angew. Chem. Int. Ed., 253, 1252-1257.

* cited by examiner

*Primary Examiner* — Narayan K Bhat
(74) *Attorney, Agent, or Firm* — Law Offices of Albert Wai-Kit Chan, PLLC

(57) ABSTRACT

The invention relates to a microarray design of hybrid upconversion nanoparticles on a nanoporous anodized alumina membrane heterogeneous assay for simultaneous detection of multiple oligonucleotides, for example, oligonucleotides from different types of viruses.

15 Claims, 3 Drawing Sheets

HETEROGENEOUS MICROARRAY BASED HYBRID UPCONVERSION NANOPROBE/NANOPOROUS MEMBRANE SYSTEM

FIELD OF THE INVENTION

The invention relates to a microarray design of hybrid upconversion nanoparticles on a nanoporous anodized alumina membrane heterogeneous assay for simultaneous detection of multiple oligonucleotides.

BACKGROUND OF THE INVENTION

The present and well-known technology for DNA oligonucleotide (oligo) detection is reverse transcription polymerase chain reaction (RT-PCR) and enzyme-linked immunosorbent assay (ELISA). The techniques are essential for identifying virus genes in one sample. Firstly, the RT-PCR technique is a genetic diagnostic technique based on cloning expressed genes by reverse transcribing the RNA of virus into its DNA complement and amplification of the complement DNA (c-DNA) via thereto-cycling in a thermos cycler. This technology involves the sophistically-designed primers for efficient amplification via nucleic acid hybridization. The readout is done by using gel electrophoresis. The whole process may require 1-3 days for accurate results. The ELISA technique is a solid-stale colorimetric immunoassay, which is based on antibody-antigen interaction via the viruses surface protein. Initially, the antigen is anchored on the substrate and a specific type of antibody linked with enzyme is added to the substrate. The interaction of the antigen and the antibody will form a complex to produce color change. As a result, the antibody expressed on the surface of virus can be identified by such technique. However, PCR requires well-trained personnel for operating the thermocycler and the amplification process is relatively time-consuming. The amplification steps are prone to contamination during successive steps. On the other hand, ELISA kits are commercialized and available from many suppliers. The kits consist of necessary chemicals and substrate for testes. However, the procedures of ELISA are laborious and the limit of detection is relatively low (nanomolar range). Owing to these shortcomings, the quest for searching sensitive and quick diagnostic assays is still on-going.

In recent years, luminescent assays are drawing attention because of their high sensitivity and the ease of making portable devices for on-site biodetections. Luminescent assays are divided into homogeneous and heterogeneous assays. Homogeneous assays are liquid phase test, and they are usually performed in micro-centrifuge tubes and simple mixing steps are required to observe the results. On the other hand, heterogeneous assays are more sensitive than homogeneous assay because of the higher binding affinity between the probe and analyte. One of the key features is the use of a solid phase substrate for detection. The results in both assays can be interpreted by using a portable light source and simple optical detectors, such as CMOS or CCDs. Therefore, they are much simpler than PCR and ELISA techniques. Nowadays, downconversion (DC) or downshifting (DS) luminescence-based assays are being reported for rapid luminescent detections. However, such luminescence mechanisms require the use of high energy light sources, such as ultraviolet (UV). It is a common knowledge that UV is harmful to DNAs and it will destroy chemical oligo chain backbones. Moreover, UV will induce autofluorescence, which will contribute to false-positive detection signals. As a result, upconversion luminescence (UCL) assays are developed to overcome the above-mentioned drawbacks. UCL is a unique luminescent phenomenon that involves sequential absorption of lower energy photons to emit a higher energy photon. In this regard, the low energy excitation can reduce the photodamage to biological samples to a minimum. Moreover, it is easier to distinguish the luminescent detection signal because of the large anti-stoke shift and the invisible near infrared (NIR) excitation. Despite UCL requires the use of lasers, the availability of cheap and portable diode lasers has overcome the issue.

The upconversion nanoparticles (UCNPs) can be obtained by hydrothermal method. The advantages are simplicity and ease of manipulation because water dispersible UCNPs with amine ($NH_2$) surface is readily obtained via a one-step hydrothermal method. However, it is relatively time consuming, requiring about 24 h of reaction time for completion, and the resultant $NH_2$-UCNPs are not regular in shape.

The UCNPs $BaGdF_5$:Yb/Er has been disclosed for homogeneous detection of Avian Influenza Virus H7 subtype (Small 2014, 10, 2390-2397) and heterogeneous detection of Ebola virus oligonucleotide (ACS Nano 2016, 10, 598-605). The UCNP of $BaGdF_5$:Yb/Er was synthesized by hydrothermal method, and the detection scheme was suitable for single target only. Since the emission intensity of $BaGdF_5$:Yb/Er is weak and the nanoparticle is not dispersing very well in water, it is difficult to control their position during the fabrication of the microarray for simultaneous detection of multi-targets.

In addition, structural engineering of core-shell upconversion nanoparticles (csUCNPs) has emerged as a powerful means to integrate functionalities and regulate the complex interplay of lanthanide interactions. The csUCNPs can be obtained by thermal decomposition method and co-precipitation synthesis.

The core-shell $NaGdF_4$:Yb/Er@$NaGdF_4$:Yb/Nd has been disclosed for in vitro and in vivo imaging (ACS Nano 2013, 7, 7200-7206), prepared by thermal decomposition method. The limitations of thermal decomposition method disclosed in the ACS Nano 2013 paper mainly arise from the synthetic route that involves the use of excessive chemicals, such as oleylamine, steps for formation of lanthanide trifluoroacetates and the need to filter the unwanted insoluble materials, which will contaminate the reaction medium. Moreover, the high reaction temperature at 310° C. for synthesis of the core-shell $NaGdF_4$:Yb/Er@$NaGdF_4$:Yb/Nd is undesirable.

The core multishell structured nanoparticles of $NaGdF_4$:Yb,Er@$NaYF_4$:Yb@$NaGdF_4$:Yb,Nd and $NaGdF_4$:Yb,Er@$NaYF_4$:Yb@$NaGdF_4$:Yb,Nd@$NaYF_4$@-$NaGdF_4$:Yb,Tm@$NaYF_4$ were prepared by co-precipitation method for in vivo imaging (Angew. Chem. Int Ed. 2016, 128, 2510-2515). The oleate core-UCNPs was first prepared and then purified to grow the multishell UCNPs. The resultant multiple shell UCNPs involved $NaGdF_4$:Yb/Er as core and $NaGdF_4$:Yb/Nd as intermediate shell. However, the size of these UCNPs is about 45-85 nm which is too large for fabrication of microarray.

There are a lot of viruses that infect different human organs and cause diseases. Some fatal viral infections have become tremendous public health issues worldwide. Early diagnosis for adequate treatment is therefore essential for fighting viral infections. Microarray technology involving core-shell UCNPs can solve the limitation of the PCR method and can be effectively applied to molecular medicine. Microarray can be employed to detect multiple viruses simultaneously, serving as a clinical tool for characterizing viral co-infections in patients.

SUMMARY OF THE INVENTION

The present invention relates to a microarray design of hybrid UCNPs on a nanoporous anodized alumina membrane heterogeneous assay for simultaneous detection of multiple oligonucleotides. The design can be generalized for detecting different types of oligonucleotides by simply modifying the surface recognition probe of upconversion nanoprobe and the microarray can detect several types of oligonucleotides at the same time.

The present invention describes a method for preparing acid modified core-shell upconversion nanoparticles, comprising the steps of: (a) preparing a first solution of one or more salts of lanthanide in oleate and 1-octadecene; (b) adding a solution of a first inorganic hydroxide and a first inorganic fluoride to said first solution; (c) purifying the solution resulting from step (b) to form a core for core-shell upconversion nanoparticles (csUCNPs); (d) preparing a second solution of said one or more salts of lanthanide in oleate and 1-octadecene; (e) adding said core from step (c), a solution of a second inorganic hydroxide and a second inorganic fluoride to said second solution from step (d) to form a shell of csUCNPs on said core; (f) purifying said csUCNPs resulting from step (e); (g) treating said csUCNPs resulting from step (f) with a solution of hydrochloric acid; and (h) adding said csUCNPs resulting from step (g) to a solution comprising an acid and a third inorganic hydroxide, thereby obtaining said acid modified core-shell upconversion nanoparticles.

The present invention relates to a microarray for detection of oligonucleotides from one or more sources, comprising: (a) a first layer of an amine functionalized nanoporous anodized alumina membrane; and (b) a second layer of a polydimethylsiloxane (PDMS) thin film with one or more wells, said second layer is laid onto said first layer; wherein said polydimethylsiloxane (PDMS) thin film forms covalent bonds with acid-modified core-shell upconversion nanoparticles (csUCNPs) obtained by the method of the present invention; and one or more $NH_2$-functionalized oligonucleotide probe sequences form covalent bonds with said acid-modified core-shell upconversion nanoparticles, wherein each of said one or more wells contains one of said one or more $NH_2$-functionalized oligonucleotide probe sequences, said probe sequences can detect oligonucleotides from one or more sources.

The present invention further discloses a method of using the microarray of the present invention to detect the presence or absence of one or more oligonucleotides from one or more sources in a subject, comprising the steps of: (a) obtaining from the subject one or more samples suspected of comprising nucleotide sequences from one or more sources; (b) treating said samples with gold nanoparticles to allow the nucleotide sequences therein to form covalent bonds with said gold nanoparticles; (c) contacting the samples from step (b) with the oligonucleotide probe sequences in the microarray of the present invention under conditions effective to form a hybrid between said oligonucleotide probe sequences and said nucleotide sequences; (d) irradiating one or more wells of said microarray with a light source; and (e) detecting emission from said wells, wherein intensity of the emission would indicate the presence or absence of one or more oligonucleotides from one or more sources.

DETAILED DESCRIPTION OF THE INVENTION

Figure 1A:
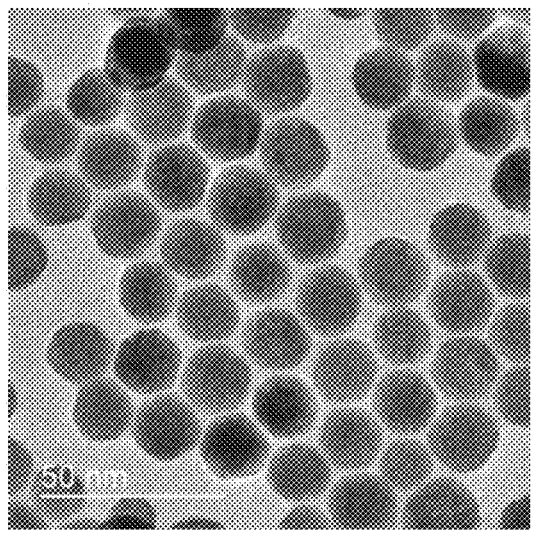
FIG. 1A shows the TEM image of amine-functionalized $NaGdF_4$:Yb/Er@$NaGdF_4$:Yb/Nd.

The present invention describes a rapid and sensitive detection method that can be easily applied to routine diagnosis. This method simultaneously detects multi specimens.

The present invention discloses a csUCNPs. The csUCNPs comprise of one or more lanthanides selected from Yttrium (Y), Ytterbium (Yb), Gadolinium (Gd), Neodymium (Nd), Lutetium (Lu). Erbium (Er). Holmium (Ho) and Terbium (Tb). In one embodiment, the csUCNPs is $NaGdF_4$:Yb/Er@$NaGdF_4$:Yb/Nd. In one embodiment, the csUCNPs is excited by a light source of 700 nm to 1000 nm. In one embodiment, the csUCNPs is excited by a light source of 980 nm. In another embodiment, the csUCNPs is excited by a light source of 808 nm.

The csUCNPs can be obtained via the growth of outer-shell layer on the core nanoparticles in co-precipitation synthesis. The size of csUCNPs are in the range of 22-27 mu. In one embodiment, the size of csUCNPs is 22 nm. In another embodiment, the size of csUCNPs is 25 nm.

The present invention describes the fabrication of a microarray of hybrid csUCNPs on a nanoporous anodized alumina membrane.

The present invention further discloses a method of using the microarray for simultaneous detection of multiple virus genes. The design can be generalized for detecting different types of virus genes by simply modifying the surface recognition probe of upconversion nanoprobe, and the microarray can detect several types of virus genes at the same time. In one embodiment, the method comprises the use of testing only lasers, the hybrid design and a detector. In one embodiment, the method comprises the use of portable diode lasers. The amount of required nanoparticles is low and the testing components are cheap. The virus gene detection time is short. In one embodiment, the detection time is 0.5-5 hours. In another embodiment, the detection time is 2 hours.

In some embodiments, the use of 808 nm instead of 980 nm lasers can pose minimal heating effect to water-based assays. Therefore, it will not induce dehybridization, and the energy efficiency is higher because 808 nm laser can penetrate deeper in samples.

In one embodiment, the method of using the microarray of the present invention can be used to detect one or more viruses, including but not limited to, influenza viruses and their subtypes, human immunodeficiency virus/AIDS (HIV/AIDS), hepatitis A virus, hepatitis B virus, hepatitis C virus, hepatitis D virus, hepatitis E virus, Ebola virus, West Nile virus and Zika Virus.

In one embodiment, one or more oligonucleotide probes can be used for simultaneous detection. In another embodiment, 1-50 oligonucleotide probes can be used for simultaneous detection. In some embodiments, 1-16 oligonucleotide probes can be used for simultaneous detection. In one embodiment, 9 oligonucleotide probes can be used for simultaneous detection.

In one embodiment, the size of nanopores of the NAAO membrane is 100 nm to 200 nm.

In one embodiment, the method comprises a specific surface modification step for anchoring the csUCNPs and AuNPs into the nanochannel of the anodized alumina membrane to establish the microarray pattern on the heterogeneous device.

In one embodiment, the present invention discloses the combination of csUCNPs and NAAO membrane to fabricate heterogeneous microarray, and method to use the microarray to detect one or more gene sequences simultaneously, for example, sequences from different viruses. The hybrid design can enhance the limit of detection compared to conventional homogeneous assay, and allow multiple virus types detection. Moreover, the microarray design can be adapted to different virus detections by modifying the sequence of the capture probe on the surface of UCNPs. The microarray can simultaneously carry out multiple hybridization reactions for the detection of multiple viruses. Therefore, the method of the present invention can shorten the detection time compared to methods that perform oligo hybridization one at a time. Moreover, the method of the present invention allows potential scaling up of detection depending on the size of the membrane.

In one embodiment, the method of the present invention can be applied to UCL based microarray assay and hybrid design of UCL and NAAO for one or more virus gene detection.

In one embodiment, the method of the present invention uses less harmful excitation sources, and utilizes NIR rather than UV for excitation. Hence, photodamage and autofluorescence effect can be minimized. Regarding sensitivity of luminescent assays, the sensitivity of conventional luminescent assay is at picomolar (pM) range while the microarray hybrid design of the present invention yielded limit of detection (LOD) at femtomolar (fM) range. In the application of csUCNPs and microarray of the present invention for multi virus DNA detection, the luminescent assays are not harmful to DNA oligos. The method of the present invention can be developed into portable luminescent assays, and the availability of hand-held and compact NIR lasers can enhance the portability of the UCL assay.

Furthermore, the portability of the method of the present invention can be easily transferred to the front line for on-site detection and the operation personnel only requires simple instruction to use the microarray. As the excitation source is a portable infrared laser pointer, the whole detection setup is very convenient. In addition, the whole detection platform can simply comprises a laser, sample holder and detector.

The cost of the present invention is lower than conventional PCR because it does not require complex instrumentation. The present device is a long-lived device with only the need to replace the NAAO for new tests. The cost can be further reduced if multiple hybridization reactions are carried out on one piece of NAAO membrane.

In one embodiment, the method of the present invention involves efficient multiple hybridization reactions which can be carried out on the NAAO membrane simultaneously. Therefore, the time for hybridization is greatly shortened. Moreover, the readout time is fast because of the use of luminescent technique.

In one embodiment, the method of the present invention can be developed for rapid screening assays for subtype testing of influenza virus.

The present invention describes a method for preparing acid modified core-shell upconversion nanoparticles, comprising the steps of: (a) preparing a first solution of one or more salts of lanthanide in oleate and 1-octadecene; (b) adding a solution of a first inorganic hydroxide and a first inorganic fluoride to said first solution; (c) purifying the solution resulting from step (b) to form a core for core-shell upconversion nanoparticles (csUCNPs); (d) preparing a second solution of said one or more salts of lanthanide in oleate and 1-octadecene; (e) adding said core from step (c), a solution of a second inorganic hydroxide and a second inorganic fluoride to said second solution from step (d) to form a shell of csUCNPs on said core; (f) purifying said csUCNPs resulting from step (e), (g) treating said csUCNPs resulting from step (f) with a solution of hydrochloric acid; and (h) adding said csUCNPs resulting from step (g) to a solution comprising an acid and a third inorganic hydroxide, thereby obtaining said acid modified core-shell upconversion nanoparticles. In one embodiment, the lanthanide is selected from the group consisting of Yttrium (Y). Ytterbium (Yb), Gadolinium (Gd), Neodymium (Nd), Lutetium (Lu), Erbium (Er), Holmium (Ho), and Terbium (Tb). In one embodiment, one or more salts of lanthanide are selected from the group consisting of chloride, trifluoroacetate and acetate. In one embodiment, the acid modified core-shell upconversion nanoparticles have a particle size ranging from 22 nm to 27 nm. In one embodiment, the acid modified core-shell upconversion nanoparticles have a particle size of 25 nm. In another embodiment, the acid modified core-shell upconversion nanoparticles have a particle size of 22 nm. In one embodiment, the core of the core-shell upconversion nanoparticles is $NaGdF_4$:Nb/Er in one embodiment, the shell of the core-shell upconversion nanoparticles is $NaGdF_4$:Yb/Nd. In one embodiment, the acid used in step (h) is polyacrylic acid (PAA).

In one embodiment, the present invention relates to a microarray for detection of oligonucleotides from one or more sources, comprising: (a) a first layer of an amine functionalized nanoporous anodized alumina membrane; and (b) a second layer of a polydimethylsiloxane (PDMS) thin film with one or more wells, said second layer is laid onto said first layer; wherein said polydimethylsiloxane (PDMS) thin film forms covalent bonds with acid-modified core-shell upconversion nanoparticles (csUCNPs) obtained by the method of present invention; and one or more $NH_2$-functionalized oligonucleotide probe sequences form covalent bonds with said acid-modified core-shell upconversion nanoparticles, wherein each of said one or more wells contains one of said one or more $NH_2$-functionalized oligonucleotide probe sequences, said probe sequences can detect oligonucleotides from one or more sources. In one embodiment, the nanoporous anodized alumina membrane is functionalized with hydrogen peroxide ($H_2O_2$) and 3-triethoxysitylpropylamine (APTES). The covalent bonds are formed by using one or more reagents selected from 1-ethyl- 3-(-3-dimethylaminopropyl) carbodiimide hydrochloride (EDC•HCl), N-hydroxysuccinimide (NHS) and 4-morpholineethanesulfonic (MES) acid. In one embodiment, the core-shell upconversion nanoparticles comprise $NaGdF_4$:Yb/Er@$NaGdF_4$:Yb/Nd. In one embodiment, the nanopore of nanoporous anodized alumina (NAAO) membrane has a size ranging from 100 nm to 200 nm. In some embodiments, the number of wells ranges from 1 to 100. In another embodiments, the number of wells ranges from 1 to 50. In some embodiments, the number of wells ranges from 1 to 16.

In one embodiment, the source is selected from the group consisting of, but not limited to, blood or blood serum, bodily fluids, urine, faeces, sputum, saliva amniotic fluid, duodenal fluid, cerebrospinal fluid, and tissue biopsy.

In one embodiment, the subject is a plant, a vertebrate, a mammal or human. In another embodiment, the oligonucleotides are derived from the group consisting of viruses, viral extracts, bacteria, yeast, fungi, parasites, allergens, cells and cell extracts. The microarray of the present invention can be used to detect viruses selected from the group consisting of influenza viruses and its subtype, human immunodeficiency virus/AIDS (HIV/AIDS), hepatitis A virus, hepatitis B virus, hepatitis C virus, hepatitis D virus, hepatitis E virus, Ebola virus, West Nile virus and Zika Virus.

The present invention further discloses a method of using the microarray of the present invention to detect the presence or absence of one or more oligonucleotides from one or more sources in a subject, comprising the steps of: (a) obtaining from the subject one or more samples suspected of comprising nucleotide sequences from one or more sources; (b) treating said samples with gold nanoparticles to allow the nucleotide sequences therein to form covalent bonds with said gold nanoparticles; (c) contacting the samples from step (b) with the oligonucleotide probe sequences in the microarray of the present invention under conditions effective to form a hybrid between said oligonucleotide probe sequences and said nucleotide sequences; (d) irradiating one or more wells of said microarray with a light source; and (e) detecting emission from said wells, wherein intensity of the emission would indicate the presence or absence of one or more oligonucleotides from one or more sources. In some embodiments, the covalent bonds are formed by using one or more reagents selected from 1-ethyl-3-(-3-dimethylaminopropyl) carbodiimide hydrochloride (EDC•HCl), N-hydroxysuccinimide (NHS) and 4-Morpholineethanesulfonic (MES) acid. In further embodiment, the wavelength of the light source ranges from 700 to 1000 nm. In certain embodiments, the limit of detection is at femtomolar range. In one embodiment, the method of method for detecting the presence or absence of one or more viruses in a subject further comprising a step of detecting emission of acid modified core-shell upconversion nanoparticles as reference to compare with the emission in step (e). The emission in step (e) is upconversion luminescence. In one embodiment, AuNPs are further modified with 11-Mercaptoundecanoic acid (MUA) or 3-mercaptopropanoic acid (3-MPA). In some embodiments, the oligonucleotides are derived from the group consisting of viruses, viral extracts, bacteria, yeast, fungi, parasites, allergens, cells and cell extracts. In certain embodiments, the viruses are selected from the group consisting of influenza viruses and its subtype, human immunodeficiency virus/AIDS (HIV/AIDS), hepatitis A virus, hepatitis B virus, hepatitis C virus, hepatitis D virus, hepatitis E virus, Ebola virus, West Nile virus and Zika Virus.

The invention will be better understood by reference to the Experimental Details which follow, but those skilled in the art will readily appreciate that the specific experiments are provided only for illustrative purpose, and are not meant to limit the invention scope as described herein, which is defined by the claims following thereafter.

Throughout this application, various references or publications are cited. Disclosures of these references or publications in their entireties are hereby incorporated by reference into this application in order to more fully describe the state of the art to which this invention pertains. It is to be noted that the transitional term "comprising", which is synonymous with "including", "containing" or "characterized by", is inclusive or open-ended, and does not exclude additional, un-recited elements or method steps.

Example 1

Synthesis and Characterization of csUCNPs $NaGdF_4$:Yb/Er@$NaGdF_4$:Yb/Nd

The synthesis of the csUCNPs $NaGdF_4$:Yb/Er@$NaGdF_4$:Yb/Nd involved the synthesis of core and subsequent coating of the shell layer.

1. Synthesis of Core UCNPs 0.4 mmol of lanthanide (Ln) acetates consisting of gadolinium, ytterbium and erbium (78 mol %, Gd, 20 mol % Yb and 2 mol % Er) were added to a three-necked flask. Then, 4 ml of oleic acid (OA) and 6 ml of 1-octadecene (1-ODE) were injected into the same flask. The mixture was mixed vigorously and heat to 100° C. for 30 min. After that, the temperature was increased to 150° C. for 1 h. After the mixture was cooled to room temperature, 1 mmol sodium hydroxide and 1.2 mmol ammonium fluoride in methanol were added to the flask. Then, the mixture was heated to 50° C. for 30 min until no bubbles were observed. The temperature was increased to 100° C. and degassed for 10 min. The medium was then protected by argon gas and heated to 290° C. for 1.5 h. After cooling to room temperature, the crude UCNPs were purified by using cyclohexane and ethanol under centrifugation. The final product was dispersed in cyclohexane for shell coating.

2. Synthesis of csUCNPs 0.4 mmol of lanthanide (Ln) acetates consisting of gadolinium, ytterbium and neodymium (70 mol %, Gd, 10 mol % Yb and 20 mol % Nd) were added to a three-necked flask. 4 ml OA and 6 ml 1-ODE were added to the flask. The mixture was mixed vigorously and heat to 100° C. for 30 min. After that, the temperature was increased to 150° C. for 1 h. After the mixture was cooled to room temperature, the as-dispersed core-UCNPs were injected to the mixture. The 1 mmol sodium hydroxide and 1.2 mmol ammonium fluoride in methanol were added to the flask. Then, the mixture was heated to 50° C. for 30 min until no bubbles were observed. The temperature was increased to 100° C. and degassed for 10 min. The medium was then protected by argon gas and heated to 290° C. for 1.5 h. After cooling to room temperature, the crude csUCNPs were purified by using cyclohexane and ethanol under centrifugation. The final product was dispersed in cyclohexane for hydrophilicity modifications.

3. Ligand-Free Modification of csUCNPs 1 ml of the as-dispersed csUCNPs in cyclohexane was added to concentrated hydrochloric acid and ethanol. The resultant mixture was sonicated for 10 mM, the mixture was centrifuged at 14,000 rpm for 30 min. After discarding the supernatant, the procedures were repeated for twice and the ligand-free csUCNPs were dispersed in water for storage.

4. Polyacrylic Acid Modification of the Ligand-Free csUC-NPs to Form PAA-csUCNPs 50 mg polyacrylic acid (PAA) powder was added to 4 ml deionized (DI) water with 1 ml 0.2 M sodium hydroxide solution until the solution became transparent. 10 mg ligand-free csUCNPs were subsequently added to the mixture. The mixture was stirred overnight and purified by high speed centrifugation to afford PAA-csUCNPs.

5. Amine Fractionalization of csUCNPs 10 mg ligand-free csUCNPs were added to 9 ml DI water and mixed for 10 min. Then, 100 µL poly(allyamine) (PAAm) was injected to the solution under sonication. The mixture is stirred for 24 h and then purified by DI water under high speed centrifugation to afford amine functionalized csUCNPs.

Figure 1B:
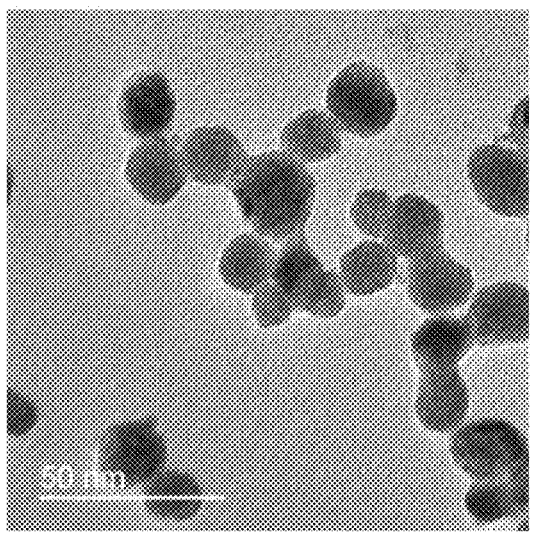
FIG. 1B shows the TEM image of core $BaGdF_5$:Yb/Er UCNPs.
Figure 2:
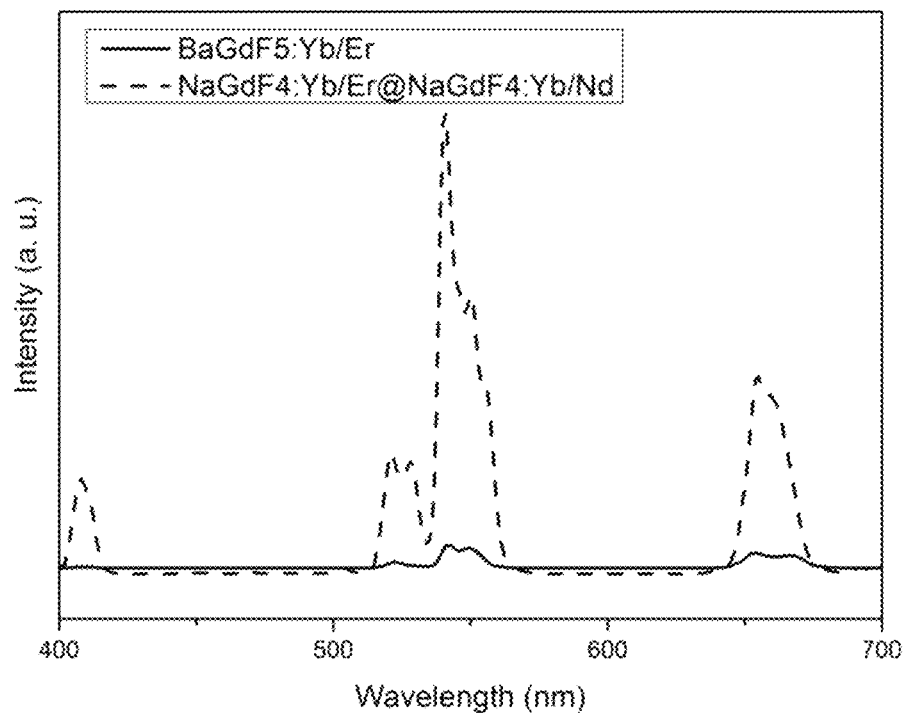
FIG. 2 shows a comparison of the UC emission spectra of amine-functionalized $NaGdF_4$:Yb/Er@$NaGdF_4$:Yb/Nd (dashed line) and core $BaGdF_5$:Yb/Er UCNPs (solid line) under 980 nm laser excitation.

6. Comparison of the Amine Functionalized Core-Shell $NaGdF_4$:Yb/Er@$NaGdF_4$:Yb/Nd with core $BaGdF_5$:Yb/Er The amine functionalized csUCNPs indicated superior properties, such as dispersity, luminescent intensity and shape uniformity over the core UCNPs. Firstly, FIG. 1A and FIG. 1B show the transmission electron microscopy (TEM) images of amine functionalized csUCNPs ($NaGdF_4$:Nb/Er@$NaGdF_4$:Yb/Nd) and core UCNPs ($BaGdF_5$:Yb/Er UCNPs) respectively. The shape of the amine functionalized core-shell UCNPs are regular and circular with size of 22 nm (FIG. 1) while the core UCNPs are irregular (FIG. 2). Moreover, the core-shell UCNPs exhibit better dispersity than the $BaGdF_5$:Yb/Er UCNPs. It is clear that the amine functionalized csUCNPs presented higher size homogeneity and water dispersity than the core UCNPs.

Apart from dispersity, the amine functionalized csUCNPs also showed improved luminescent properties over the core UCNPs. FIG. 2 depicts the upconversion (UC) emission spectra of the amine functionalized csUCNPs (dashed line) and core UCNPs (solid line). The comparison showed stark contrast between the emission intensity of the amine functionalized csUCNPs and core UCNPs. The overall emission of the amine functionalized csUCNPs is higher than that of core UCNPs. It was estimated that the emission intensity of the amine functionalized csUCNPs was 20 times higher than that of the core UCNPs. This is due to the difference in material system, phase and structure. The hexagonal phase provides more asymmetric characters while core-shell structure of the $NaGdF_4$:Yb/Er@$NaGdF4$:Yb/Nd passivates the defects on the particle surfaces. This accounts for the enhanced emission peaks. These peaks are the intrinsic property of $Er^{31}$ ions, the doping of this ions yield these characteristic peaks.

Example 2

Fabrication of the Microarray Based on Upconversion Nanoparticle/Nanoporous Anodized Alumina Membrane

1. Amine Functionalization of Nanoporous Anodized Alumina Membrane

The nanoporous anodized alumina (NAAO) membrane is boiled in a solution consisting of hydrogen peroxide ($H_2O_2$) and 3-Triethoxysilylpropylamine (APTES) for 10 min. Then, the NAAO membrane is washed with acetone and dried at 100° C. for 10 min. The process is repeated for three times.

2. Fabrication of Microarray by Covalent Coupling Reaction of PAA-csUCNPs and $NH_2$-NAAO Membrane A Polydimethylsiloxane (PDMS) thin film with nine wells is used as template for coupling reactions. The dimension of each well is 2 mm and the distance between consecutive wells is also 2 min. Before injection into the wells, the PAA-csUCNPs are activated. A mixture of 2 mg PAA-csUCNPs, 2 mg 1-ethyl-3-(-3-dimethylaminopropyl) carbodiimide hydrochloride (EDC•HCl) and 3 mg N-hydroxysuccinimide (NHS) in 0.1 M 4-Morpholineethanesulfonic (MES) acid buffer at pH 3.8, is shaken for 20 min. The PDMS film is then laid onto the $NH_2$-NAAO membrane and the activated PAA-csUCNPs are injected into a well. The same steps are repeated for the remaining wells.

Example 3

Simultaneous Detection of Multiple Viruses

1. Conjugation of Probe Sequence and the PAA-csUCNPs/NAAO Membrane

The $NH_2$-functionalized probe oligonucleotide (oligo) sequence is purchased from Integrated DNA Technologies. The probe sequence is first activated via the previously mentioned covalent coupling reaction in step 2 of Example 2: 2 mg of EDC-HCl and 3 mg NHS are added to 500 µL MES buffer solution (pH 3.4). 2 nmol of the activated probe sequence is added to the membrane for conjugation with PAA-csUCNPs for 2 h. Then, the membrane is washed by DI water.

2. Capturing of Virus Oligonucleotide by Gold Nanoparticles

The 10 nm citrate-capped gold nanoparticles (AuNPs) is purchased from Sigma-Aldrich. The AuNPs are modified with MUA by mixing $5.44 \times 10^{-13}$ mol AuNPs and $1 \times 10^{-6}$ mol MUA in DI water for 2 h. The thiol-modified AuNPs (MUA-AuNPs) are collected by centrifugation and redisperse in phosphate buffer. Then, 3 mM EDC in water was added to the MUA-AuNPs in PB buffer and shakes for 20 min. The virus oligonucleotide is added into the tube for capturing reaction for 2 h. Finally, the AuNPs-virus oligonucleotide conjugate is purified by centrifugation.

3. Hybridization of Virus Oligonucleotide Bearing Gold Nanoparticles with Probe Sequence on the Amine Functionalized csUCNPs The AuNPs conjugated with different types of virus oligonucleotides are injected into the wells of the microarray in phosphate buffer saline (PBS) solution. Each well consists of one type of probe sequence. The hybridization of the probe sequence on PAA-csUCNPs and the virus oligonucleotide is carried out for 2 h. After that, PBS solution is used to rinse the wells for subsequent detection by using photoluminescent spectroscopy.

4. Simultaneous Detection of Multiple Viruses

Figure 3:
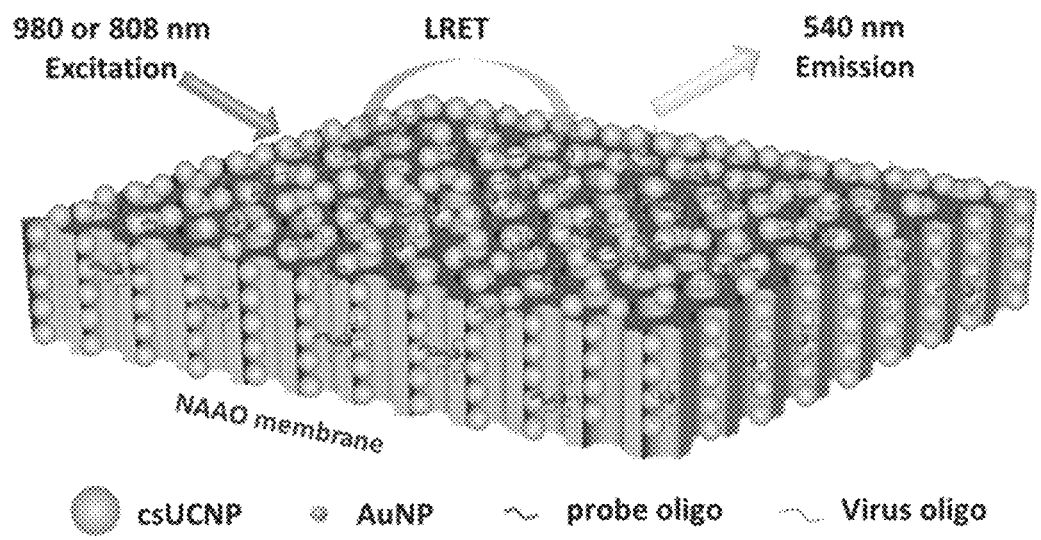
FIG. 3 is a drawing of the hybrid polyacrylic acid modified csUCNPs (PAA-csUCNPs) and nanoporous anodized alumina (NAAO) membrane detection system with virus DNA oligonucleotide-AuNPs conjugate, where the probe oligonucleotide sequence is conjugated to PAA-csUCNPs. The excitation sources are 808 nm or 980 nm laser and the green luminescence (540 nm) is transferred via LRET to the AuNPs. The quenched luminescence can be used to quantify the amount of virus DNA oligonucleotides in the sample.

As shown in FIG. 3, the PAA-csUCNPs are injected onto the amine functionalized NAAO membrane for internalization of the nanochannels of NAAO. To facilitate the microarray system, a mask will be deposited on the surface of the membrane to ensure the formation of the microarray by sequential injection of the probe sequence to the well created by the mask. After that, ligand exchange of citrate to MUA is carried out on the surface of AuNPs. The MUA-AuNPs are used to capture the virus oligonucleotide by using EDC. The virus oligonucleotide conjugated with AuNPs are added to the wells for DNA hybridization for 2 h.

Figure 4:
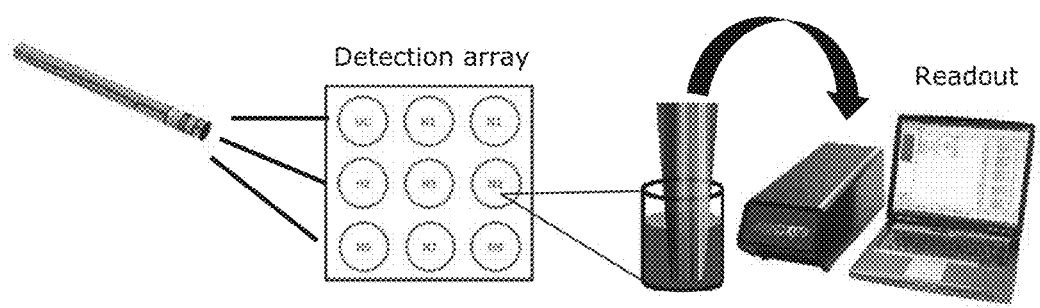
FIG. 4 is a drawing of the microarray hybrid PAA-csUCNPs/NAAO membrane detection system. The wells are examined by using the 980 nm laser pointer for changes in UCL signal. The top left corner well contains bare PAA-csUCNPs as the reference for comparison. The change in UCL can be monitored by the photodetector.

In FIG. 4, the top left hand corner is the PAA-csUCNPs for reference to compare the change in UCL intensity. The other wells are injected with UCNPs with different probe oligonucleotides, such as H1, H3, H5 and H7 influenza virus oligonucleotides. The wells are inspected by using the portable 980 nm laser pointer. If the well reports a change in UCL signal, the sample may be suspected to consist of the virus DNA oligonucleotide sequence.

REFERENCES

1. Ye, W. W.; Tsang, M.-K.; Liu, X.; Yang, M.; Hao, J. *Small* 2014, 10, 2390-2397.
2. Tsang, M.-K.; Ye, W. W.; Wang, G.; Li, J.; Yang, M.; Hao, J, *ACS Nano* 2016, 10, 598-605.
3. Wang, Y.-F.; Liu, G.-Y.; Sun, L.-D.; Xiao, J.-W.; Zhou, J.-C.; Yan, C.-H. *ACS Nano* 2013, 7, 7200-7206.
4. Li, X.; Guo, Z.; Zhao, T.; Lu, Y.; Zhao, L.; Zhao, D.; Zhang, F. *Angew. Chem. Int. Ed.* 2016, 128, 2510-2515.

What is claimed is:

1. A microarray for detection of oligonucleotides from one or more sources, comprising:
    (1) an amine functionalized nanoporous anodized alumina (NH2-NAAO) membrane; and
    (2) a polydimethylsiloxane (PDMS) thin film with one or more wells, wherein said PDMS thin film is laid onto said NH2-NAAO membrane;
    wherein said NH2-NAAO membrane is covalently bonded with acid-modified core-shell upconversion nanoparticles (csUCNPs) conjugated with one or more oligonucleotide probe sequences for detecting said oligonucleotides from one or more sources, wherein said acid-modified csUCNPs are circular in shape, range from 22 nm to 27 nm in size, and comprise NaGdF4:Yb/Er@NaGdF4:Yb/Nd.

2. The microarray of claim 1, wherein said NH2-NAAO membrane is obtained by functionalizing nanoporous anodized alumina membrane with hydrogen peroxide (H2O2) and 3-triethoxysilylpropylamine (APTES).

3. The microarray of claim 1, wherein said NH2-NAAO membrane is covalently bonded with said acid-modified csUCNPs by using one or more reagents selected from 1-ethyl-3-(-3-dimethylaminopropyl) carbodiimide hydrochloride (EDC•HCl), N-hydroxysuccinimide (NHS) and 4-morpholineethanesulfonic (MES) acid.

4. The microarray of claim 1, wherein said nanoporous anodized alumina membrane has a nanopore size ranging from 100 nm to 200 nm.

5. The microarray of claim 1, wherein the number of wells ranges from 1 to 16.

6. The microarray of claim 1, wherein the oligonucleotides from one or more sources are derived from the group consisting of viruses, viral extracts, bacteria, yeast, fungi, parasites, allergens, cells and cell extracts.

7. The microarray of claim 6, wherein said viruses are selected from the group consisting of influenza viruses and its subtype, human immunodeficiency virus/AIDS (HIV/AIDS), hepatitis A virus, hepatitis B virus, hepatitis C virus, hepatitis D virus, hepatitis E virus, Ebola virus, West Nile virus and Zika Virus.

8. A method for preparing acid modified core-shell upconversion nanoparticles which comprise NaGdF4:Yb/Er@NaGdF4:Yb/Nd, are circular in shape, and range from 22 nm to 27 nm in size, comprising the steps of:
    (a) preparing a first solution of one or more salts of lanthanides Gd, Yb and Er in oleic acid and 1-octadecene;
    (b) adding a solution of a first inorganic hydroxide and a first inorganic fluoride to said first solution;
    (c) purifying the solution resulting from step (b) to form a core for core-shell upconversion nanoparticles (csUCNPs), said core comprising NaGdF4:Yb/Er;
    (d) preparing a second solution of said one or more salts of lanthanides Gd, Yb and Nd in oleic acid and 1-octadecene;
    (e) adding said core from step (c), a solution of a second inorganic hydroxide and a second inorganic fluoride to said second solution from step (d) to form a shell of csUCNPs on said core, said shell comprising NaGdF4:Yb/Nd;
    (f) purifying said csUCNPs resulting from step (e);
    (g) treating said csUCNPs resulting from step (f) with a solution of hydrochloric acid; and
    (h) adding said csUCNPs resulting from step (g) to a solution comprising an acid and a third inorganic hydroxide, thereby obtaining said acid modified core-shell upconversion nanoparticles.

9. The method of claim 8, wherein said one or more salts of lanthanides are selected from the group consisting of chloride, trifluoroacetate and acetate.

10. The method of claim 8, wherein said acid is polyacrylic acid (PAA).

11. A method of using the microarray of claim 1 to detect the presence or absence of one or more oligonucleotides from one or more sources in a subject, comprising the steps of:
    (a) obtaining from the subject one or more samples suspected of comprising nucleotide sequences from one or more sources;
    (b) treating said samples with gold nanoparticles to allow the nucleotide sequences therein to form covalent bonds with said gold nanoparticles;
    (c) contacting the samples from step (b) with the oligonucleotide probe sequences in the microarray of claim 8 under conditions effective to form a hybrid between said oligonucleotide probe sequences and said nucleotide sequences;
    (d) irradiating one or more wells of said microarray with a light source; and
    (e) detecting emission from said wells, wherein intensity of the emission would indicate the presence or absence of one or more oligonucleotides from one or more sources.

12. The method of claim 11, wherein said light source emits wavelength ranging from 700 to 1000 nm.

13. The method of claim 11, further comprising a step of detecting emission of acid modified core-shell upconversion nanoparticles as reference to compare with the emission in step (e).

14. The microarray method of claim 11, wherein the oligonucleotides are derived from the group consisting of viruses, viral extracts, bacteria, yeast, fungi, parasites, allergens, cells and cell extracts.

15. The microarray method of claim 14, wherein said viruses are selected from the group consisting of influenza viruses and its subtype, human immunodeficiency virus/AIDS (HIV/AIDS), hepatitis A virus, hepatitis B virus, hepatitis C virus, hepatitis D virus, hepatitis E virus, Ebola virus, West Nile virus and Zika Virus.

* * * * *

UNITED STATES PATENT AND TRADEMARK OFFICE
CERTIFICATE OF CORRECTION

PATENT NO. : 10,266,403 B2
APPLICATION NO. : 15/442850
DATED : April 23, 2019
INVENTOR(S) : Jianhua Hao et al.

It is certified that error appears in the above-identified patent and that said Letters Patent is hereby corrected as shown below:

On the Title Page

In (56) References Cited, under OTHER PUBLICATIONS:

In the first publication, please replace "Infl uenza" with --Influenza--

In the second publication, please replace "J.ACS Nano" with --ACS Nano--

In the fifth publication, please replace "MnO2" with --$MnO_2$--

In the sixth publication, please replace "LiLuF4" with --$LiLuF_4$--

In the Specification

Column 3, Line 16, please replace "oleate" with --oleic acid--

Column 3, Line 21, please replace "oleate" with --oleic acid--

Column 6, Line 16, please replace "oleate" with --oleic acid--

Column 6, Line 21, please replace "oleate" with --oleic acid--

Column 9, Line 9, please replace "Amine Fractionalization" with --Amine Functionalization--

Column 9, Line 44, please replace "NaGdF4" with --$NaGdF_4$--

Column 9, Line 47, please replace "$Er^{31}$" with --$Er^{3+}$--

Column 10, Line 7, please replace "pH 3.8" with --pH 3.4--

Signed and Sealed this
Ninth Day of July, 2019

Andrei Iancu
*Director of the United States Patent and Trademark Office*

CERTIFICATE OF CORRECTION (continued)
U.S. Pat. No. 10,266,403 B2

In the Claims

Column 11, Claim 1, Line 18, please replace "(NH2-NAAO)" with --(NH$_2$-NAAO)--

Column 11, Claim 1, Line 21, please replace "NH2-NAAO" with --NH$_2$-NAAO--

Column 11, Claim 1, Line 22, please replace "NH2-NAAO" with --NH$_2$-NAAO--

Column 11, Claim 1, Line 28, please replace "NaGdF4" with --NaGdF$_4$--

Column 11, Claim 1, Line 29, please replace "NaGdF4" with --NaGdF$_4$--

Column 11, Claim 2, Line 30, please replace "NH2-NAAO" with --NH$_2$-NAAO--

Column 11, Claim 2, Line 32, please replace "H2O2" with --H$_2$O$_2$--

Column 11, Claim 3, Line 34, please replace "NH2-NAAO" with --NH$_2$-NAAO--

Column 11, Claim 8, Line 56, please replace "NaGdF4" with --NaGdF$_4$--

Column 11, Claim 8, Line 57, please replace "NaGdF4" with --NaGdF$_4$--

Column 12, Claim 8, Line 3, please replace "NaGdF4" with --NaGdF$_4$--

Column 12, Claim 8, Line 10, please replace "NaGdF4" with --NaGdF$_4$--

Column 12, Claim 11, Line 36-37, please replace "claim 8" with --claim 1--